United States Patent [19]

Kutilin

[11] Patent Number: 4,835,471
[45] Date of Patent: May 30, 1989

[54] MEASURING DEVICE WITH OSCILLATION CIRCUIT INCLUDING AN EXCITING COIL AND TUNED TO A SPECIFIC RESONANT FREQUENCY, FOR DETERMINING CONTENT OF MAGNETIZABLE SUBSTANCES IN MATERIALS

[75] Inventor: Paul Kutilin, Kapfenberg, Austria

[73] Assignee: Boehler Ges.m.b.H., Vienna, Austria

[21] Appl. No.: 119,090

[22] Filed: Nov. 12, 1987

[30] Foreign Application Priority Data

Nov. 12, 1986 [AT] Austria ................ 3006/86

[51] Int. Cl.$^4$ ............... G01R 33/12; G01N 27/72
[52] U.S. Cl. ............................. 324/236; 324/234
[58] Field of Search ........... 324/204, 233, 234, 236, 324/237, 327, 377

[56] References Cited

U.S. PATENT DOCUMENTS

| | | | |
|---|---|---|---|
| 2,576,173 | 11/1951 | Cornelius | 324/236 |
| 2,587,631 | 3/1952 | Kuehne | 324/234 X |
| 3,201,774 | 8/1965 | Uemura | 324/327 X |
| 3,473,110 | 10/1969 | Hardin et al. | 324/236 |
| 3,473,111 | 10/1969 | Leersnijder et al. | 324/236 |
| 3,477,018 | 11/1969 | Richardson et al. | 324/236 X |
| 3,686,563 | 8/1972 | Walter | 324/377 |
| 3,808,524 | 4/1974 | Tarassoff et al. | 324/236 |
| 3,896,371 | 7/1975 | Hametta | 324/327 |
| 3,996,510 | 12/1976 | Guichard | 324/236 X |
| 4,210,864 | 7/1980 | Miyakawa et al. | 324/236 X |
| 4,473,799 | 9/1984 | Favre | 324/236 X |

FOREIGN PATENT DOCUMENTS 1006543 10/1965 United Kingdom .............. 324/236

*Primary Examiner*—Gerard R. Strecker
*Attorney, Agent, or Firm*—Holman & Stern, Chartered

[57] ABSTRACT

A measuring device for determining the content of magnetizable substances, particularly ferrite and martensite, in a sample, the device including an exciting coil which preferably has an iron core, for producing a magnetic field to be applied to the sample, and further including an evaluation circuit and a display device for displaying measurement quantities proportional to the content of magnetizable substances in the sample. To improve measurement accuracy, the exciting coil is a part of a tuned resonant oscillation circuit. The inductance of the exciting coil can be changed by the magnetic field induced in the sample as a result of the applied magnetic field, whereby the change in inductance results in a change in the resonant frequency of the oscillation circuit. The measurement quantity fed to the display device is a quantity proportional to the content of magnetizable substances and corresponds to the change in at least one of the parameters of the oscillation circuit which change results when the resonant frequency is changed.

21 Claims, 5 Drawing Sheets

MEASURING DEVICE WITH OSCILLATION CIRCUIT INCLUDING AN EXCITING COIL AND TUNED TO A SPECIFIC RESONANT FREQUENCY, FOR DETERMINING CONTENT OF MAGNETIZABLE SUBSTANCES IN MATERIALS

BACKGROUND AND SUMMARY OF THE INVENTION

The invention relates to a measuring device for determining the content of magnetizable substances, particularly ferrite and margensite, in a sample, the measuring device including an exciting coil which preferably has an iron core, for producing a magnetic field to be applied to the sample, and further including an evaluation circuit and a means for displaying measurement quantities proportional to the content of magnetizable substances in the sample.

The content (proportion) of magnetizable substances in given samples or workpieces can be determined by known methods such as metallographic examination, X-ray diffraction, testing the saturation magnetization, application of magnetic scales (balances), calculations from analysis of the Schaeffler diagram, use of a magnetic ferrite measuring device employing the eddy current principle such as the Type 1053 from the firm of Foerster, or the Type M 10 B from the firm of Fischer, and by other conventional methods.

The content of magnetizable substances, particularly the content of ferrite as a structural constituent thereof which may be undesirable or may be required in rather large percentage amounts depending on the type of material, must often be determined reliably, for quality control reasons. For practical applications, the measurement method should be free of susceptibility to interference, should be rapid, and should be applicable to, e.g., solid samples.

Metallographic, X-ray diffraction, magnetic scale, and saturation magnetization measurement methods are cumbersome, subject to interference, and often completely unusable for particular samples. Known portable measuring devices enable interference-free ferrite measurements, but for higher ferrite contents they are susceptible to experiencing systematic error.

A known ferrite-measuring device (that from the firm of Foerster) is comprised of a device with a contacting element for engaging the sample, operating elements, and display means. The contacting element is a ferromagnetic rod which bears two coils. One coil (primary coil) is excited by an a.c. current and induces an EMF in the secondary coil (secondary winding), according to the law of induction $$e = k.w.f. \Phi.$$

When the rod is applied to a sample with a particular ferrite content, the magnetic flux is changed correspondingly. Because the other parameters are unchanged, an EMF proportional to the ferrite content of the sample is generated.

By appropriate calibration, this EMF can be made proportional to the ferrite content of the probe, within a particular narrow range of correlated values.

However, in order to produce a substantial measurement signal, it is necessary to have a substantial change in the magnetic flux $\Phi$, because of the transformer law (i.e., Faraday's law). And because $\Phi$ is a function of B (magnetic induction, as may be seen from FIG. 1), and the relative permeability $\mu_r$ is linked with B, the operating region of this measuring device lies in the low field strength region ($\leq 4$ A/cm). However, this is the region of high slope of the magnetization lines, hence high $\mu_r$, and as a result of the high curve slope the measurement accuracy is still quite high. Nonetheless, as shown in FIG. 2, at the relatively low field strengths of known measuring devices there can occur intersection of the characteristic curves of the relative permeability $\mu_r$, which can lead to errors in the registered values.

At relatively high frequencies of the exciting magnetic field of the measuring probe (e.g., 2 kHz), the measured values are influenced by the electrical conductivity of the sample material. As studies have shown, these errors (resulting from eddy currents induced in the sample by the exciting field) are negligible only at frequencies $\leq 500$ Hz. The eddy current losses increase with conductivity and frequency, and have an undesirable effect on the measuring circuit.

It is thus an underlying object of the present invention to provide a measuring device wherein the electrical conductivity of the sample material has a negligible effect on the measurement results, and whereby the contents (proportions) of magnetizable substances between 0% and 100% can be determined accurately. In addition, errors relating to engagement of the sample by the device should be kept low, and the effects of magnetization present in the sample should be substantially eliminated. In addition, it is desirable for the field strength of the exciting magnet to intersect the magnetization lines beyond the bend in the curve as shown in FIG. 2, where the trend of the magnetization curves has a regular relation to the content of magnetizable substances.

These objects are met by the measuring device of the present invention in which the exciting coil is a part of an oscillation circuit tuned to a specific resonant frequency and preferably operated at a selected operating point; further, the magnetic parameters of the exciting coil, particularly its inductance, are variable by means of the magnetic field, which variation determines a new resonant frequency of the oscillation circuit; and still further, the variation of at least one of the parameters of the oscillation circuit (e.g., current, voltage, and/or frequency), which variation is associated with a variation in the resonant frequency of the oscillation circuit, is expressed as a measurement quantity which is proportional to the content of magnetizable substances.

The measuring device according to the present invention enables the content of magnetizable substances in the entire range (0-100%) to be determined very accurately, because the exciting coil is part of a tuned resonant circuit, and the resonant frequency of a resonant circuit reacts very sensitively to variations in its parameters. A simple calibration measurement can be performed with the exciting coil not in contact with the sample, whereby the null point of the measurement is exactly established. The end point of the scale is established using a sample comprised 100% of a magnetizable substance (e.g. pure ferrite).

According to a preferred embodiment of the invention, the oscillation circuit comprises the exciting coil, a capacitor, and a coupling coil for introducing the operating frequency of the oscillation circuit, with the exciting coil, capacitor, and coupling coil being connected in a series resonant connection. It is advantageous under this arrangement if the value selected as the measurement value for the evaluation circuit is the voltage drop across the exciting coil. According to an alternative embodiment, the oscillation circuit comprises the exciting coil, a capacitor, and a coupling coil for introducing the operating frequency of the oscillation circuit, connected in a parallel resonant circuit, wherein the value selected as the measurement value for the evaluation circuit is the rate of increase of the voltage in the oscillation circuit, or the voltage drop across a resistance inserted between the capacitor and the exciting coil. The embodiments are of simple construction, durable in operation, relatively temperature-insensitive, and accurate in measurement.

One can obtain large measurement ranges of the measurement values obtained from the resonant circuit if the operating frequency selected for the series or parallel resonant circuit is disposed in the frequency range of maximum slope on a side (flank) of the resonance curve.

Another embodiment of the invention is characterized in that an oscillation circuit is comprised of the exciting coil and a capacitor in parallel or in series with it, which circuit is coupled to a LF (low frequency) generator and/or forms a part of the LF generator, wherein the frequency of the oscillation circuit is variable due to interaction with the sample. It is provided that the oscillation circuit is tuned to a specific resonant frequency, and the measurement value employed for the evaluation circuit is the frequency variation occurring in the oscillation circuit when the inductance of the exciting coil is changed. This measurement device of complex design can be made very sensitive, and can provide very accurate measurement results.

Preferably, the field strength of the magnetic field applied to the sample from the exciting coil is between 20 and 200 A/cm, particularly between 30 and 100 A/cm. When magnetic fields of this magnitude are employed, errors attributable to details of the engagement of the sample by the contacting element do now play as great a role as when weaker magnetic fields are employed. In addition, ordinary residual magnetization in the sample is erased or rendered of negligible effect on the measurement. Also, the lines of magnetization measured are in a regular pattern with regard to different magnetizable substances (e.g. ferromagnetic, ferritic, etc.).

In applying such magnetic fields, it is advantageous if the exciting coil surrounds a contacting core, preferably ferritic, which is to engage the sample, and if the exciting coil is in turn surrounded by a preferably cylindrical magnet yoke, with one end of this yoke connected with the contacting core, and the contacting core extending beyond the other end of the yoke. This enables a convenient contacting element to be constructed which can make good contact with the sample, and the magnetic flux of the contacting element can be caused to accurately and substantially engage the sample.

For evaluating the signal, it is a simple matter to insert a bridge rectifier and a bandpass filter as the evaluation circuit for the measurement signal ahead of the display means.

BRIEF DESCRIPTION OF THE DRAWINGS

The invention will be described in more detail hereinbelow, with reference to the Figures.

DETAILED DESCRIPTION OF THE INVENTION

Figure 1:
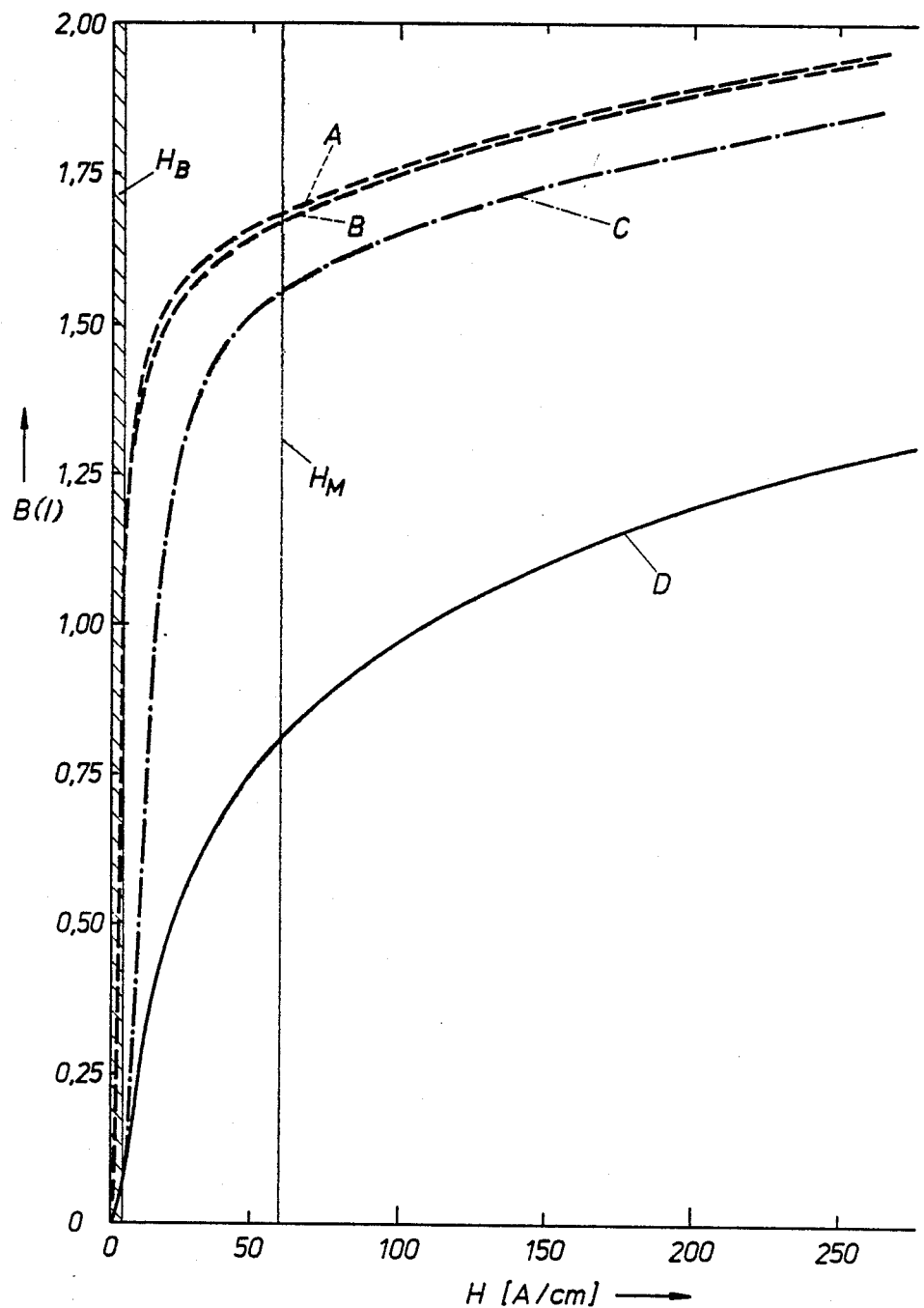
FIG. 1 is a diagram showing lines of magnetization.

FIG. 1 shows the relationship between the field strength applied to a sample and the magnetic flux. Here curves A and B are characteristic of unalloyed steel, C of electrolytic iron, and D of duplex steel (2-phase steel). $H_B$ indicates the field strength range for known ferrite-measuring devices, and $H_M$ that for the measurement device of the present invention. It will be seen that at the field strengths at which the known devices operate there is a low-angle intersection with the lines of magnetization.

Figure 2:
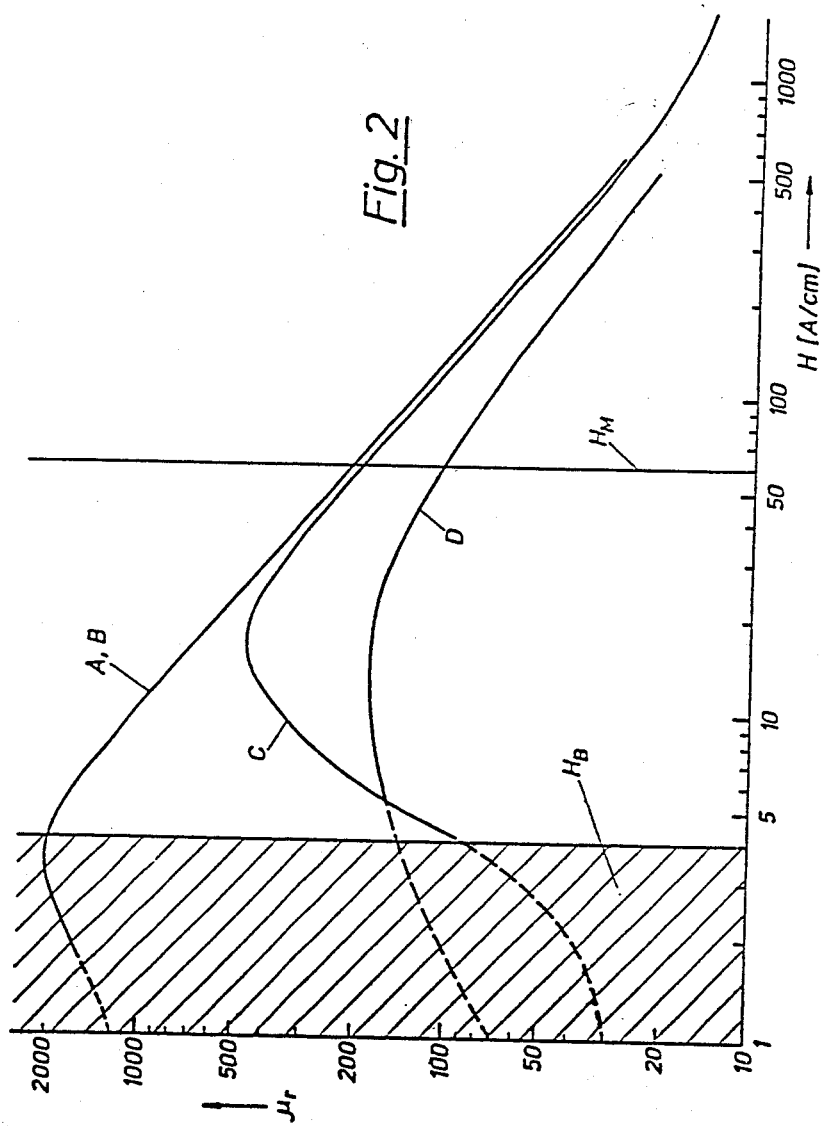
FIG. 2 is a diagram showing permeability curves.

FIG. 2 is a diagram of relative permeability $\mu_r$ plotted against the field strength H of the exciting magnetic field ($H_B$, $H_M$) applied to the sample.

The permeability curves intersect (e.g. the curves for electrolytic iron and duplex steel) in the range of low-measuring magnetic field strengths. Accordingly, at such low field strengths errors can occur in evaluating the measurement results. But with the measuring magnetic field strength $H_M$ of the present device, such errors do not occur, because the individual permeability curves are well ordered with respect to relative permeability. In FIG. 1 the lines of magnetization are presented as new curves and original curves.

Figure 3:
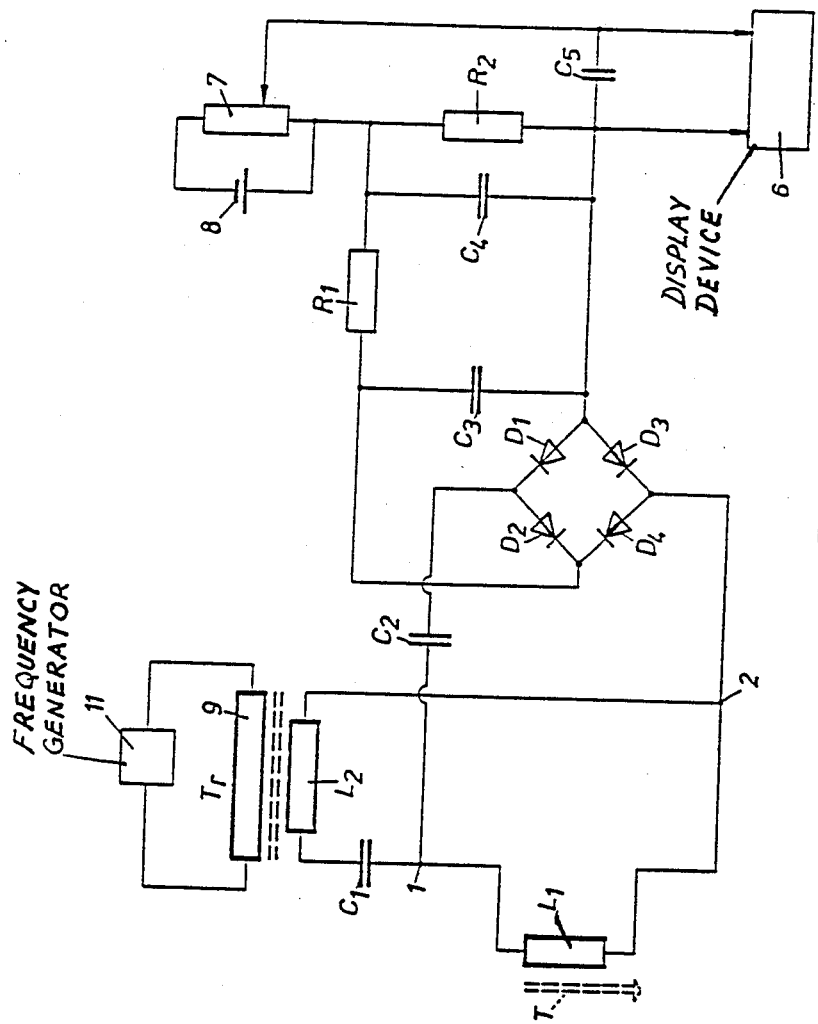
FIG. 3 is a circuit diagram showing a measuring device according to the present invention.

FIG. 3 illustrates a principal exemplary embodiment of a measuring device according to the invention. An exciting coil L1 of a contacting element T forms a series resonant circuit with a capacitor C1 and and inductor L2, which series resonant circuit has a specific resonant frequency. A coupling transformer Tr with a primary winding 9 and inductor L2 as a secondary winding and fed by a frequency generator 11 is employed to introduce the selected operating frequency via inductor L2 into the resonant circuit L1-C1-L2. This operating frequency is within the "resonance range", i.e. is within the range of frequencies in which resonance behavior occurs in the resonant circuit. Advantageously, resonant frequencies of around 400–1500 Hz are chosen, with operating frequencies of around 100–400 Hz. For a resonant frequency of around 500 Hz, the operating frequency is preferably around 200 Hz.

Preferably the frequency and voltage of the frequency generator are held constant, to the extent possible.

The measurement signal derived from such a series resonant circuit is taken from the voltage drop across the exciting coil L1 at points 1 and 2. The measurement signal is passed via a coupling capacitor C2 and a diode bridge D1-D4 to a filter section comprised of components C3, R1, C4, R2, and C5, and thence to the display device 6. Device 6 is supplied with power by a battery 8 via a potantiometer 7, providing a variable voltage for null balance.

Figure 7:
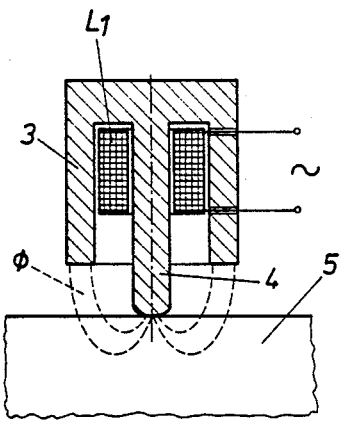
FIG. 7 is a schematic representation of the structure of a contacting element with exciting coil according to the present invention.

The measuring device of the present invention makes use of the change in the inductance of the coil L1 which occurs when coil L1 engages a sample 5, as in FIG. 7. This exciting coil L1 is disposed on or around a ferritic contacting element core 4, with an exemplary arrangement shown in FIG. 7. When no sample (other than air) is engaged by the contacting element core 4, one can register, from the oscillation circuit, the curve for 0% ferrite content shown in FIG. 4, with the operating frequency being changed as indicated. For a given inductance of the exciting coil L1, a given inductance of the secondary winding L2, and a given capacitance of the capacitor C1, the current in the exciting coil is $I_o$ at the selected measuring (operating) frequency $Hz_M$. This current $I_o$ corresponds to a ferrite content of 0%. The selected operating frequency which defined the operating point is advantageously below the resonant frequency, in order to minimize eddy current influences on the measurement result. Such influences occur in measurements taken at higher frequencies. Therefore, according to the invention, measurements are made at frequencies in the region of the left flank (side) of the resonance curves. $Hz_M$ (FIG. 4) is the measurement frequency supplied to the resonant circuit from the transformer coil 9.

Figure 4:
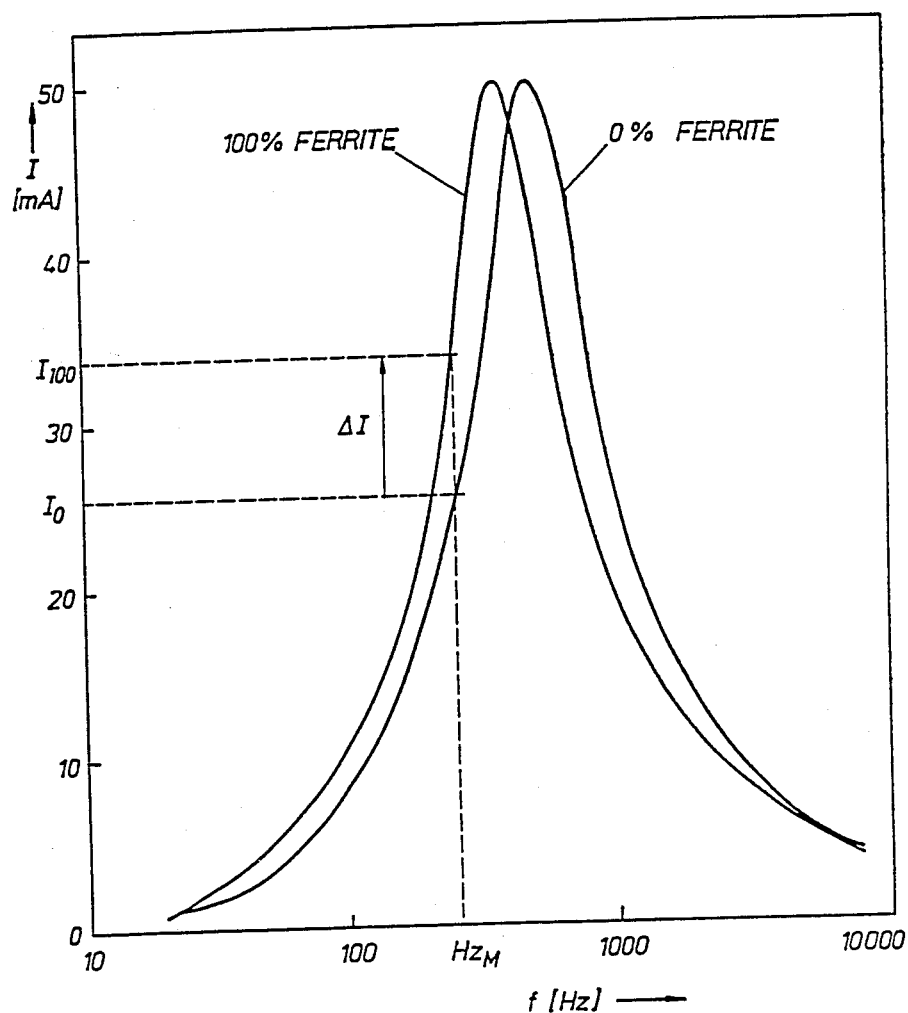
FIG. 4 is a plot indicating the measurement signal.

If a sample 5 containing a magnetizable substance is engaged by the exciting coil L1, the changed inductance of the coil L1 causes a change in the resonance conditions of the series resonant ciruict. As a result, the resonant frequency is decreased, as illustrated in FIG. 4 for the engagement of a sample comprised 100% of ferrite. The measurement signal for 100% ferrite corresponds to the current $I_{100}$ in the exciting coil L1 at the selected operating frequency $Hz_M$. The difference $I_{100} - I_o$ corresponds to the measurement range for a content of magnetizable substance of between 0% and 100% (the magnetizable substance here being ferrite).

When a measurement is made on a sample with, e.g., 50% ferrite content, a resonance curve will be produced which lies between the curves for 0% and 100% ferrite, and which intersects with the operating frequency line $Hz_M$ at a point therealong proportional to the current corresponding to a 50% ferrite content in the sample.

In this manner, the measuring device can be accurately calibrated by a plurality of measurements at different ferrite contents.

The measurement principle underlying the device of the present invention is that when an exciting coil L1 engages only air, the resonant frequency of the series resonant circuit is determined essentially only by the inductance of the coil L1, in that C1 and L2 have fixed values. The inductance of the exciting coil is determined by the number of windings in the coil and by the magnetic parameters of the magnetizable part of the contacting element T, particularly the parameters of the ferritic core (contacting element core) 4 of the contacting element T. When a sample 5 is engaged by the core 4 as shown in FIG. 7, the magnetic field induced by the magnetic flux Φ in the sample 5 changes the inductance of the exciting coil L1, whereby the resonance conditions and resonant frequency of the series resonant circuit are changed.

Figure 5:
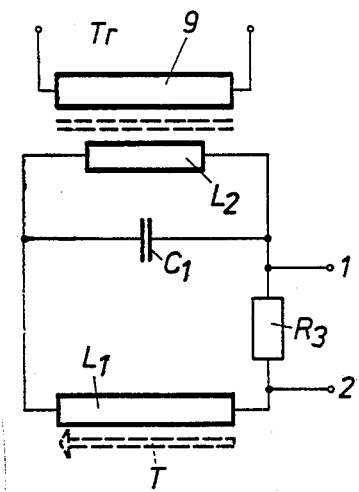
FIG. 5 is a circuit diagram of a parallel resonant circuit for a measuring device according to the present invention.

FIG. 5 illustrates a similar measurement principle, with a parallel resonant circuit being used instead of a series circuit as in FIG. 3. The parallel circuit in FIG. 5 is comprised of the exciting coil L1, capacitor C1, and transformer secondary winding L2. The resonance behavior of the parallel circuit essentially corresponds to that of a series circuit. The measurement signal is taken at points 1 and 2 of a resistance R3 connected between the exciting coil L1 and the capacitor C1.

Figure 6:
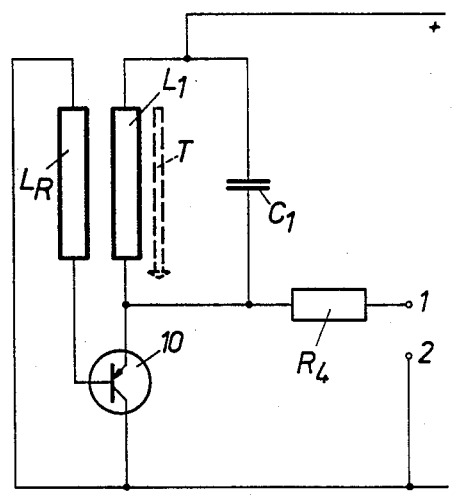
FIG. 6 is a circuit diagram of an oscillation circuit which is coupled to a LF generator and forms a part of the LF generator according to the present invention.
Figure 6A:
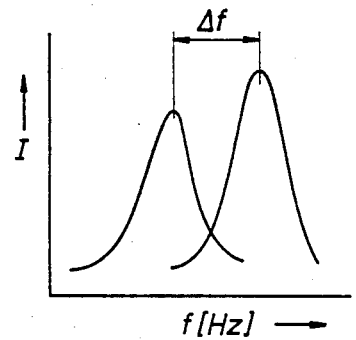
FIG. 6a is a plot indicating the measurement signal.

FIG. 6 illustrates an embodiment in which the exciting coil L1 forms an oscillation circuit with the contacting element T and the capacitor C1, which oscillation circuit is part of a low frequency (LF) generator including a transistor 10 and a feedback coil $L_r$. The resonant circuit L1-C1 is driven into a resonant oscillating mode with the aid of the transistor 10 and the feedback coil $L_R$. When the inductance of the exciting coil L1 is changed upon engaging a sample containing a magnetizable substance, the frequency of the oscillation circuit decreases, as illustrated in FIG. 6a. The measurement signal comprises the change in frequency measured at points 1 and 2 (before and after the occurrence of the engagement of the sample respectively), making use of a resistance R4.

The difference in the frequencies measured for 0% ferrite content (i.e., the exciting coil L1 engaging air) and for 100% magnetizable substance content (i.e., the exciting coil L1 contacting, e.g., 100% ferrite), establishes the scale range of measurements for the measuring device.

FIG. 7 illustrates schematically the structure of a contacting element T. The core 4 of the element is surrounded by the exciting coil L1 which in turn is surrounded by a magnet yoke 3. The magnetic field lines Φ emanating from the contacting element core 4 and penetrating into the sample 5 are depicted. These lines return to the yoke 3, establishing a closed magnetic circuit.

Advantageously, the operating frequency for the oscillation circuit is chosen such that the variations in the measured parameter are in the flank (side) regions of the resonance curves, whereby there is a relative large change in the parameter in response to a change in the content of magnetizable substance in the sample, i.e. the flank regions are regions of high slope.

The present measuring device may be used for all magnetizable substances, i.e. for ferromagnetic, martensitic, ferritic, and all other magnetizable or magnetic substances.

It will be appreciated that other types of electronic evaluation means may be used in place of the diode bridge D1-D4; e.g., a frequency discriminator may be employed.

It is advantageous that with the measuring device of the present invention, when the inductance of the exciting coil L1 is changed by engagement with a magnetizable sample 5, the current through the inductor L1 increases, in the process providing increased voltage drop across the exciting coil, and thereby simplifying the measurement. Because the measurement is made in regions of high and increasing slope on the resonance curves, precise measurement is possible particularly in regions of high contact of magnetizable substances.

Table 1 presents the results of measurements on a group of ferrite samples, first using metallographic evaluation with a ruled grating; next, employing model M 10B measuring devices supplied by the firm of Fischer, with three-point and single-point calibration; and finally using a measuring device according to the present invention. It may be seen that the measurement results obtained with the device of the present invention agree well with those obtained by metallographic evaluation, and indeed they agree extremely well in ranges of high ferrite content, whereas with the conventional eddy current devices there are substantial deviations from the metallographic data.

With the high field strength employed (e.g., 60 A/cm) with the present measuring device, the measured magnetic parameters of the samples lie in the relatively low-slope region of the B vs. H curve. However, in this region the relative permeability is directly proportional to the content of magnetizable substances in the sample material, so that the measurement quantities will have a regular and readily determinable relationship.

TABLE 1

Measurement Tests on a Group of Ferrite Samples of Qualities A 903-So and A 905-So

| Melt Sample | Sample no. | Specific resistance, | Metallographic ferrite evaluation via ruled gating | Measured values with Fischer M10B, with three-point calibration (2.7%, 9.6%, and 29.6%) | Measured values with Fischer M10B, with single-point calibration (viz., at 100%) | Measured values with measuring device of present invention |
|---|---|---|---|---|---|---|
| 10468 | 6 | 0.869 m | 39.9% | 43.1 ± 1% | 42.3% | 41.2 ± 0.4% |
| 10683 | 7 | 0.849 m | 44.3% | 45.2 ± 0.6% | 43.2% | 46.3 ± 0.4% |
| 10463 | 8 | 0.888 m | 45.9% | 48.9 ± 1.8% | 45.9% | 45.9 ± 0.8% |
| 10462 | 9 | 0.880 m | 68.6% | 76.7 ± 3.1% | 74.9% | 69.1 ± 1.0% |
| 10466 | 10 | 0.842 m | 71.7% | 64.8 ± 1.9% | 63.0% | 72.0 ± 1.4% |
| 10461 | 11 | 0.908 m | 86.2% | 101.3 ± 2.4% | 95.9% | 88.2 ± 1.3% |
| 10681 | 12 | 0.720 m | 93.4% | 85.5 ± 2.5% | 82.5% | 91.2 ± 1.1% |
| 10460 | 13 | 0.885 m | 97.9% | 91.0 ± 5.3% | 87.9% | 97.4 ± 1.7% |

What is claimed is:

1. A measuring device for determining the content of magnetizable substances such as ferrite, martensite and the like in a sample, comprising:
   a contacting element for contacting the sample, which contacting element includes an exciting coil means for producing a magnetic field to be applied to the sample to induce a magnetic field in the sample, the exciting coil having an iron core and being fed by a frequency generator;
   an evaluation circuit means operably connected with the exciting coil for evaluating measurement values corresponding to the inductance of the exciting coil and for providing measurement quantities corresponding thereto, said measurement quantities being proportional to the content of magnetizable substances in the sample; and
   display means operably connected with the evaluation circuit means for displaying measurement quantities provided from the evaluation circuit means; wherein:
   the exciting coil is a part of an oscillation circuit tuned to a specific resonant frequency, the oscillation circuit being operated at a selected operating frequency in the range between 100 and 400 Hz, over which selected operating frequency range said oscillation circuit exhibits resonant behavior at frequencies in the range between 400 and 1,500 Hz;
   magnetic parameters of the exciting coil, including its inductance, are variable in response to a magnetic field induced in the sample as a result of the magnetic field applied to the sample by the exciting coil, which variation in the magnetic parameters of the exciting coil determines a new resonant frequency of the oscillation circuit shifted from said specific resonant frequency, the field strength of the magnetic field applied to the sample by the exciting coil being in the range between 20-200 A/cm; and
   variation in at least one parameter of the oscillation circuit from the group of parameters including current, voltage and frequency, which variation in at least one parameter of the oscillation circuit is associated with a variation in the resonant frequency of the oscillation circuit due to said variation in the magnetic parameters of the exciting coil, is displayed by the display means as a measurement quantity which is proportional to the content of magnetizable substances in the sample.

2. A measuring device according to claim 1, wherein the oscillation circuit is comprised of the exciting coil, a capacitor, and a coupling coil for introducing the selected operating frequency into the oscillation circuit, said exciting coil, capacitor and coupling coil being connected in a series resonant circuit configuration.

3. A measuring device according to claim 1, wherein the measurement value evaluated by the evaluation circuit means is the voltage drop across the exciting coil.

4. A measuring device according to claim 1, wherein the oscillation circuit is comprised of the exciting coil, a capacitor, and a coupling coil for introducing the selected operating frequency into the oscillation circuit, said exciting coil, capacitor and coupling coil being connected in a parallel resonant circuit configuration.

5. A measuring device according to claim 4, wherein the measurement value evaluated by the evaluation circuit means is the current in the oscillation circuit.

6. A measuring device according to claim 4, wherein the measurement value evaluated by the evaluation circuit means is the voltage drop across a resistance connected between the capacitor and the exciting coil.

7. A measuring device according to claim 1, is formed by the exciting coil and a capacitor connected wherein the oscillation circuit in parallel with said exciting coil, the oscillation circuit being coupled to a low frequency generator, whereby the frequency of the oscillation circuit can be varied by engagement of the exciting coil with a sample.

8. A measuring device according to claim 7, wherein the oscillation circuit forms a part of the low frequency generator.

9. A measuring device according to claim 1, wherein the oscillation circuit is formed by the exciting coil and a capacitor connected in series with said exciting coil, the oscillation circuit being coupled to a low frequency generator, whereby the frequency of the oscillation circuit can be varied by engagement of the exciting coil with a sample.

10. A measuring device according to claim 9, wherein the oscillation circuit forms a part of the low frequency generator.

11. A measuring device according to claim 7, wherein the oscillation circuit is tuned to a specific resonant frequency, and the measurement value evaluated by the evaluation circuit means is the frequency variation occurring in the oscillation circuit when the inductance of the exciting coil is changed.

12. A measuring device according to claim 9, wherein the oscillation circuit is tuned to a specific resonant frequency, and the measurement value evaluated by the evaluation circuit means is the frequency variation occurring in the oscillation circuit when the inductance of the exciting coil is changed.

13. A measuring device according to claim 1, wherein the exciting coil surrounds a contacting core adapted to engage the sample, said exciting coil in turn being surrounded by a magnetic yoke with one end of said magnetic yoke being connected to the contacting core, and the contacting core extends beyond the other end of said yoke.

14. A measuring device according to claim 13, wherein the contacting core is ferritic.

15. A measuring device according to claim 13, wherein the magnetic yoke is cylindrical.

16. A measuring device according to claim 1, wherein the evaluation circuit means is comprised of a bridge rectifier and a bandpass filter connected between the oscillation circuit and the display means.

17. A measuring device according to claim 1, wherein the selected operating frequency of the oscillation circuit is a frequency in the frequency domain of the very high-slope flank region of the resonance curve of the tuned resonance of the oscillation circuit.

18. A measuring device according to claim 1, wherein the field strength of the magnetic field applied to the sample by the exciting coil is in the range of 30-100 A/cm.

19. A measuring device according to claim 1, wherein the field strength of the magnetic field applied to the sample by the exciting coil is in the range of 50-70 A/cm.

20. A measuring device according to claim 1, wherein the selected operating frequency of the oscillation circuit is in the range of 100-300 Hz.

21. A measuring device according to claim 1, wherein the selected operating frequency of the oscillation circuit is approximately 200 Hz.

* * * * *